United States Patent [19]

Eichen et al.

[11] Patent Number: 4,590,031
[45] Date of Patent: May 20, 1986

[54] MOLDING TOOL AND METHOD

[75] Inventors: Erwin Eichen, West Bloomfield; James D. Flasck, Rochester, both of Mich.

[73] Assignee: Energy Conversion Devices, Inc., Troy, Mich.

[21] Appl. No.: 597,438

[22] Filed: Apr. 6, 1984

Related U.S. Application Data

[63] Continuation-in-part of Ser. No. 535,352, Sep. 23, 1983.

[51] Int. Cl.[4] .................... B29C 33/00; B29C 41/42
[52] U.S. Cl. .................... 264/338; 65/374.11; 65/374.13; 249/134; 264/219; 427/34
[58] Field of Search ............... 65/26, 374.11, 374.13; 427/34; 249/114 R, 115, 134; 204/192 C, 192 R, 192 SP, 192 D; 264/338, 219

[56] References Cited

U.S. PATENT DOCUMENTS

| | | | |
|---|---|---|---|
| 3,108,900 | 10/1963 | Papp | 204/192 C |
| 3,244,497 | 4/1966 | Copeland | 65/26 |
| 3,671,306 | 6/1972 | Allen | 428/336 |
| 3,867,191 | 2/1975 | Galasso et al. | 428/389 |
| 3,967,029 | 6/1976 | Veltri et al. | 428/408 |
| 4,017,587 | 4/1977 | Ditter et al. | 423/291 |
| 4,120,930 | 10/1978 | Lemelson | 249/114 R |
| 4,146,654 | 3/1979 | Guyonnet | 427/34 |
| 4,175,611 | 11/1979 | Fletcher | 427/34 |
| 4,225,355 | 9/1980 | Galasso et al. | 106/43 |
| 4,251,254 | 2/1981 | Klomp et al. | 65/374.13 |
| 4,287,259 | 9/1981 | Riley et al. | 428/408 |
| 4,476,151 | 10/1984 | Keller et al. | 427/34 |

FOREIGN PATENT DOCUMENTS

| | | | |
|---|---|---|---|
| 3206322 | 12/1982 | Fed. Rep. of Germany. | |
| 2039879 | 8/1980 | United Kingdom | 65/26 |

OTHER PUBLICATIONS

Vossen et al., Thin Film Processes, Academic Press, N.Y. 1978, pp. 48 & 49.
Roth et al., Chemical Abstracts, vol. 93 (1980), No. 59239h.
Voigt, et al., Chemical Abstracts, vol. 98 (1983), No. 220127k.
Fitzer, et al., Chemical Abstracts, vol. 99 (1983), No. 126797c.

*Primary Examiner*—Willard E. Hoag
*Attorney, Agent, or Firm*—James D. Ryndak; Lawrence G. Norris; Richard M. Goldman

[57] ABSTRACT

A coating and method of depositing it is provided. The wear resistant coating comprises a thin layer of disordered boron and carbon applied to a substrate. The coating has good adherence and provides good resistance to wear so that it is useful as a tool coating. In a more specific embodiment, the coating is disordered boron carbide. The coating can have a high gloss and can also be used as a decorative coating.

The coating can be made by sputtering boron and carbon onto a substrate. A bias voltage may be applied to the substrate during sputtering.

In accordance with one embodiment, the disordered boron and carbon coating is of a composition $B_xC_{1-x}$ where x is from about 0.60 to about 0.90.

In accordance with another embodiment, an improved molding tool is provided that includes a disordered carbon coating on at least a portion of the working surface of the molding tool. The coating provides improved release characteristics, longer tool life and results in molded articles having smoother finishes and improved detail.

34 Claims, 11 Drawing Figures

MOLDING TOOL AND METHOD

RELATED APPLICATION

This application is a continuation-in-part application of U.S. Ser. No. 535,352, filed Sept. 23, 1983 entitled "Disordered Coating and Method."

BACKGROUND

This invention relates to coatings and more particularly to coatings on surfaces that are subjected to friction or wear and to coatings for tools utilized for cutting, forming and grinding.

In the past, tools and articles that are subject to wear have been fabricated to achieve various hardness, lubricity and wear characteristics by controlling certain parameters. For example, tools for working and shaping unhardened steels may be fabricated from steel containing enough carbon to form very hard martensite. In more complicated compositions, varying the carbon content and alloy content makes possible non-deforming steels, shock-resistant steels, hot-work steels, or high-speed steels. In some of these steels, alloying elements such as titanium, vanadium, molybdenum, tungsten and chromium are used. These are elements which have a great affinity for carbon and form hard, wear-resistant metallic carbides. However, in many cases, it it desirable to provide a tool having a coating on the surface thereof to improve the hardness and/or lubricity of the tool. This is especially the case where it is desired to lengthen the tool life or increase productivity, or where it is necessary to shape and work hardened steel, for example. However, many types of wear resistant coatings require high temperatures for application, thereby making them impractical for use on many types of substrate materials, since the properties of the substrate may change significantly under such temperatures. Other types of coatings do not adhere sufficiently to the substrate under working conditions.

Thus, a need exists for a wear resistant coating that can be applied at relatively low temperature to avoid significant change of substrate properties. A need exists for a wear-resistant coating for articles, such as tools, to provide increased life. A need also exists for a wear resistant coating that has improved adhesion properties and resistance to fracture.

In a more specific application, it would be desirable to provide an improved mold tool to lengthen mold tool life, improve release characteristics, and improve the surface finish and detail of molded items.

SUMMARY OF THE INVENTION

In accordance with a broad aspect of the invention, a disordered boron and carbon coating is provided that exhibits excellent resistance to wear. As used herein, resistance to wear includes resistance to erosion, oxidation, corrosion, wear from frictional contact and similar phenomena. Tools and other articles which are subject to wear, such as a result of contact with other surfaces, can be coated with the disordered boron and carbon material to increase the useful life of the tool or article. The coating can be disordered boron carbide or a mixture of disordered boron and carbon.

The coating is formed as a thin layer on the surface of an article such as a tool or other substrate and preferably comprises a coating of boron carbide. As used herein, "substrate" and "article" are interchangeable and can include a coating or coatings other than a coating of the invention.

Tools coated in accordance with the invention utilizing disordered boron and carbon generally have excellent hardness and lubricity characteristics which result in increased lifetimes and depending on the particular application, improved surface finishes on parts or workpieces machined therewith.

As used herein, a "disordered coating of boron and carbon" shall be understood to be amorphous, polycrystalline (and lacking long range order), microcrystalline or a mixture of any combination of those phases.

Preferably the composition of the coating is:

$B_xC_{1-x}$, where "B" represents boron, "C" represents carbon and "x" and "1−x" represent the relative amount of boron and carbon respectively, present in the coating, "x" being from about 0.60 to about 0.90. A disordered coating of boron and carbon on either side of this range is also included within the scope of the invention. Most preferably, the coating is disordered boron carbide ($B_4C$). Thus, included in accordance with the present invention are coatings which are non-stoichiometric as well as those that are.

The coating of the present invention is disordered when formed. It is believed that a disordered wear resistant coating performs better than a single phase crystalline coating. A disordered coating may be more susceptible than a single phase crystalline coating to diffusive bonding between the substrate surface and the coating, resulting in better adherence. Disordered materials also lack extended lattice planes through which fractures can propagate and in general can withstand relatively high deformation forces without fracture. Such materials are generally less susceptible to adverse chemical attack, such as corrosion and oxidation, than a single phase crystalline material. It is believed that the foregoing advantages are more fully realized with an amorphous or substantially amorphous coating.

In accordance with the invention, a nonstoichiometric disordered wear resistant coating is provided in which the amount of boron and carbon present in the coating composition can be varied to achieve desired characteristics while avoiding the formation of extended lattice planes present in non-disordered materials which could adversely affect the adherence, wear resistance or other properties of the coating.

Any suitable method to form the disordered coating can be used. One method of forming the coating is by sputtering. Since sputtering can take place at a relatively low substrate temperature (generally about 200° C. or less, for example), the coating can be formed while avoiding significant changes in the properties of the substrate material while providing a surface that has increased resistance to wear and excellent lubricity. Accordingly, the invention is particularly useful for coating materials such as tool steel and tungsten carbide, for example, since the processing temperature does not degrade the properties of these materials. Sputtering at low substrate temperature also allows formation of the coating in a disordered state.

The coating can be applied to a tool surface or substrate surface as a continuous thin layer without significantly changing the dimensions of the tool since the thickness of the coating can be relatively thin and can be closely controlled. After a tool, with or without a coating, has been in use, a coating in accordance with the invention can be applied thereto, to achieve a desired tolerance or otherwise replace material that has been worn from the tool. Thus, the invention makes possible the reclamation of tools that would otherwise be discarded.

A coating in accordance with the invention can be applied directly over a substrate surface while achieving excellent adherence for use on tools and other surfaces that are subjected to wear or friction, for example. No adherence coating or layer is required, as the coating of the invention can provide excellent adherence. Preferably, the coating is continuous.

The disordered boron and carbon coating of the invention can be further characterized as being extremely inert and stable, with good resistance to degradation as a result of exposure to humidity and heat, for example.

In accordance with another aspect of the invention, a coated article is provided that includes a substrate and a wear resistant coating over at least a portion of the substrate. The coating is a disordered coating of boron and carbon as previously described.

It has been discovered that the coating in accordance with the invention is especially useful as a coating on molds, dies and the like. Providing the coating on such implements can result in longer mold life, improved release characteristics and better surface detail and smoother finishes on the resulting molded parts. The coating of the invention can be used on all types of molds or dies where a moldable or castable material is to be formed. For example, the coating may be used in connection with molds and dies for molding, injection molding and die casting. The terms "mold" and "moldable" are used in a broad sense and are meant to include "die" and "castable."

In accordance with a more specific embodiment of this aspect of the invention, a molding tool is provided that includes a disordered coating of boron and carbon as previously described on at least a portion of the working surface of the mold. Generally, the entire working surface will be coated with the disordered coating. Use of such coatings on molding tools have been found to provide significant advantages compared to uncoated molding tools. These advantages include longer mold life, improved release characteristics, and molded articles having greater detail and smoother finishes. In addition, cleaning of the mold after use is facilitated.

In accordance with another aspect of the invention, a method of molding is provided that includes molding an article with a mold tool having on at least a portion of its working surface a disordered boron and carbon coating in accordance with the invention.

In accordance with another aspect of the invention, a method is provided for making a wear resistant boron and carbon coating, which method is similar to the described general method and comprises depositing over a substrate a layer of disordered boron and carbon. The layer of disordered boron and carbon is as previously described.

In accordance with still another aspect of the invention, a method of machining a workpiece is provided. As used herein, "machining" is used in a broad sense and includes, but is not limited to, cutting, grinding, shaping, polishing, reaming, turning, drilling, broaching, sharpening and the like. The method comprises machining a workpiece with an article, such as a tool, for example, having on at least a portion of the article or on a working edge or surface thereof, coated with a wear resistant boron and carbon coating in accordance with the invention.

In accordance with another aspect of the invention, the disordered boron and carbon coatings are also useful as decorative coatings. The disordered boron and carbon coatings can be characterized as having a high gloss and an attractive gray color. Such coatings also, of course, exhibit good resistance to wear.

The color of the coating is dependent on the relative amount of boron and carbon present in the coating. Coatings with a relatively high amount of carbon will be a darker shade of gray than coatings with less carbon.

To a degree, the thickness of the coating determines the degree of grayness of the coating. The optical density of the coating is related to its thickness, until a certain thickness is achieved where a thicker coating will not provide a significant increase in optical density.

The smoothness of the substrate surface to which the coating is applied generally has an effect on the gloss of the coating. Usually, providing a smoother surface results in a coating having a higher gloss. Accordingly, where a high gloss coating is desired, the substrate surface should be relatively smooth.

Preferably, the coatings essentially contain only carbon and boron, although it is to be understood that minor amounts of impurities will almost invariably be present. Further, other elements or compounds other than carbon may be present, as long as they do not interfere with the desired color, gloss or wear resistance.

The coatings of the invention can be further characterized in being extremely inert and stable, with good resistance to color change as a result of exposure to ultraviolet radiation, for example. The coatings also exhibit good resistance to chemical attack.

Generally, when a coating of the invention is provided for decorative purposes, it will be thinner than a coating for wear resistance applications, although a thicker coating can be used for decorative purposes as desired.

DETAILED DESCRIPTION

The disordered coating of the invention is preferably formed by sputtering, although any suitable technique which forms a disordered coating of boron and carbon having suitable adherence and physical integrity can be utilized. The preferred type of sputtering is dc magnetron sputtering with a bias voltage. Sputtering allows the coating to be applied at relatively low temperatures and is less likely to affect the substrate properties than other techniques which require relatively high temperatures.

While sputter depositing techniques are generally known to those skilled in the art, to maximize the benefits of the invention, it is advantageous to form the desired coating with a sputtering technique that is adapted to the particular geometry of the surface to be coated. Usually, a dc or rf bias is applied to the substrate during application of the coating by sputtering. The bias may improve adhesion of the coating formed on the substrate, reduce stress in the coating and increase the density of the coating. The substrate geometry in part determines the most desirable sputtering technique for a particular application.

Prior to sputter depositing, it is important to provide an atomically clean surface on the portion of the tool or substrate surface that is to be coated (as used in this specification, "substrate" means that portion of a tool or substrate exclusive of a coating or coatings in accordance with the invention). This facilitates the formation of a uniform coating which adheres to the substrate surface. There are several methods known to those skilled in the art for providing an atomically clean surface for sputtering and any such method may be utilized. The following surface preparation method is provided by way of example only and is not to be construed as a limitation upon the present invention.

In accordance with one method for providing an atomically clean substrate surface, the substrate is degreased with a chlorinated hydrocarbon degreaser. Thereafter, the substrate is rinsed in methanol and is then subjected to either plasma or dry chemical etching. When plasma etching is utilized, preferably a fluorinated carrier gas, such as carbon tetrafluoride is utilized. The carrier gas decomposes and provides fluorine which cleans the substrate surface. The final step for providing an atomically clean surface for the coating is sputter etching in an argon plasma.

After an atomically clean surface has been provided on the substrate or at least on that portion of the substrate which is to be coated, the coating can be applied.

Where a high gloss coating is desired, usually for decorative purposes, the surface will preferably be relatively smooth, since this is believed to facilitate the formation of a high gloss coating. Some surfaces will already be smooth and no treatment is required. Where a smoother surface is desired, any suitable means can be utilized. For example, the surface may be polished. Alternatively, the surface may be precoated with a layer or layers of polymer material such as a thermoplastic or thermosetting polymer resin or other material which can provide a relatively smooth surface. Epoxy and acrylic resins are examples of such polymer materials. A combination of polishing and applying a precoat layer can also be utilized.

Generally, the coating is applied by sputtering. The preferred sputtering conditions depend on surface geometry and the type of microstructure desired. Generally, however, it is desirable for the surface of the coating to be smooth, especially for many wear-related applications. The internal microstructure of the disordered coating may be columnar or non-columnar. For some applications, a columnar surface of the coating can be desirable.

When it is desired to produce a columnar microstructure, any type of sputtering technique known in the art which produces a columnar microstructure can be utilized. One technique for producing a columnar microstructure applies sufficient bias voltage to the substrate to cause formation of the columnar microstructure. For some coating materials and/or substrate geometries, a columnar microstructure may not be formed, even with a high bias voltage. As is known to those skilled in the art, bias sputtering is the process of maintaining a negative bias voltage on the substrate during deposition.

By applying a bias voltage to the substrate, the density, purity, adhesion and internal stress of the coating can be controlled. Generally, application of a bias voltage tends to increase the density, purity and adhesion and also tends to decrease the internal stress of the coating.

The bias voltage applied to a substrate during sputtering may be varied in a desired sequence. The preferred bias sequencing depends on the substrate geometry and the desired microstructure. For complex shapes, or for surfaces having a relatively high (about 2.0 or greater) aspect ratio (which is the ratio of the macroscopic depth to the width of a surface, e.g. the aspect ratio of a planar surface is 0 and the aspect ratio of a surface having a depression whose depth equals its width is 1), it is desirable to initially sputter the coating material onto the substrate at a relatively low bias voltage (for example, about $-100$ to $-200$ volts) to insure complete coverage. Thereafter, the bias voltage is increased to a relatively high bias voltage (for example, about $-1000$ to $-2500$ volts). The biasing voltage can be gradually increased (ramp increased) or step increased. Utilizing such a bias voltage tends to promote a more dense, purer coating having greater adhesion, less internal stress and also tends to promote columnar growth. It is believed that a columnar microstructure generally results in better adherence, possibly as a result of mechanical anchoring to the substrate. For the exterior coating surface applied to a surface with a high aspect ratio, the bias voltage can be applied as for the underlying portion of the coating, except that if a smooth surface is desired, towards the end of the deposition the bias voltage is lowered (for example, generally to about $-100$ to $-200$ volts) or eliminated, which tends to allow formation of a smooth surface.

For a surface having an aspect ratio of about 0.5 to about 2.0, the coating is preferably sputtered at essentially a constant bias voltage, generally between $-500$ and $-1000$ volts. A higher voltage can be used. For the exterior portion of the coating, the bias voltage should be adjusted such that a relatively smooth surface is provided, if this is desired.

For a surface having a relatively low aspect ratio (between 0 and about 0.5), preferably the bias voltage initially is higher (about $-1000$ to $-2500$ volts) and can be decreased to low voltage (about $-100$ to $-200$ volts) in either step or ramp fashion, or eliminated. Again, the decrease or elimination of bias voltage usually applies towards the end of the deposition of the coating. A decreasing or a relatively low bias voltage also tends to promote a relatively smooth surface which generally results in a more lubricious surface, which can be desirable in many cases.

Since sputtering can take place at relatively low substrate temperatures (generally about 200° C. or less, for example), the coatings can be formed while avoiding significant changes in the properties of the substrate material while providing a surface that has increased resistance to wear and excellent lubricity. Accordingly, the invention is particularly useful for coating materials such as tool steel, aluminum, brass, chrome, nickel, tungsten carbide and cemented carbides, graphite, glass, natural and synthetic polymers and other substrates that can be adversely affected by elevated temperature, for example, since the processing temperature does not degrade the properties of these materials. Sputtering at low substrate temperatures also allows formation of the coatings in a disordered state. The invention is also suitable for coating precisely dimensioned substrates, regardless of substrate composition.

To produce sputtered disordered coatings, generally the sputtering will take place at substrate surface temperatures of less than about 200° C. and usually at about 100° C. or even less, to facilitate formation of disordered coatings. Thus, the coatings in accordance with the present invention can be formed at relatively low temperatures. The target generally is also cooled to prevent evaporation, melting or other unwanted degradation of the target. As a result, the coating is applied to a tool surface, for example, without significantly altering physical properties of the tool, such as the dimensions, hardness and transverse rupture strength. Generally, substrate temperatures, target compositions, deposition rates and gas pressures which tend to prevent the formation of disordered coatings should be avoided.

For decorative uses, the thickness of the coating can be varied and no minimum thickness is required. However, it is desirable for the thickness of the coating to be in the range of from about 2000 Å to about 5000 Å (10,000 Å = 1 micrometer). Coatings which are thinner will be more transparent and the grayness of the coating will be less. Coatings thicker than 5000 Å can be utilized, but for decorative uses, cost may be a limiting factor. The coatings are preferably thick enough to be substantially non-transparent.

For wear resistance, it is usually desirable to form a coating that is between about one (1) and about eight (8) micrometers in thickness, with a thickness of about 2.5 micrometers usually being a good thickness for use on tools. Coatings having a thickness in excess of about eight (8) micrometers may not be particularly desirable in applications where high tolerance must be maintained since the geometry and/or size of the tool and parts resulting therefrom may be altered. The sputtering technique can be chosen in accordance with the guidelines previously set forth relating to relatively simple and complex substrate surface geometries.

It is to be understood that the coatings and methods described herein can be utilized on tools that have been subjected to use, either with or without the coatings described herein. For example, after a tool having a coating or coatings in accordance with the invention has been in use, and is either worn or outside of a desired tolerance range, the same type of coating or another type of coating in accordance with the invention can be applied to the tool, resulting in an increased tool life. Also, a coating can be applied to tools which did not previously have a coating of the invention thereon. Thus, tools which would otherwise be discarded can be reclaimed.

Referring now to FIGS. 1-11, several types of articles are illustrated which can be coated in accordance with the present invention.

Figures 1, 2:
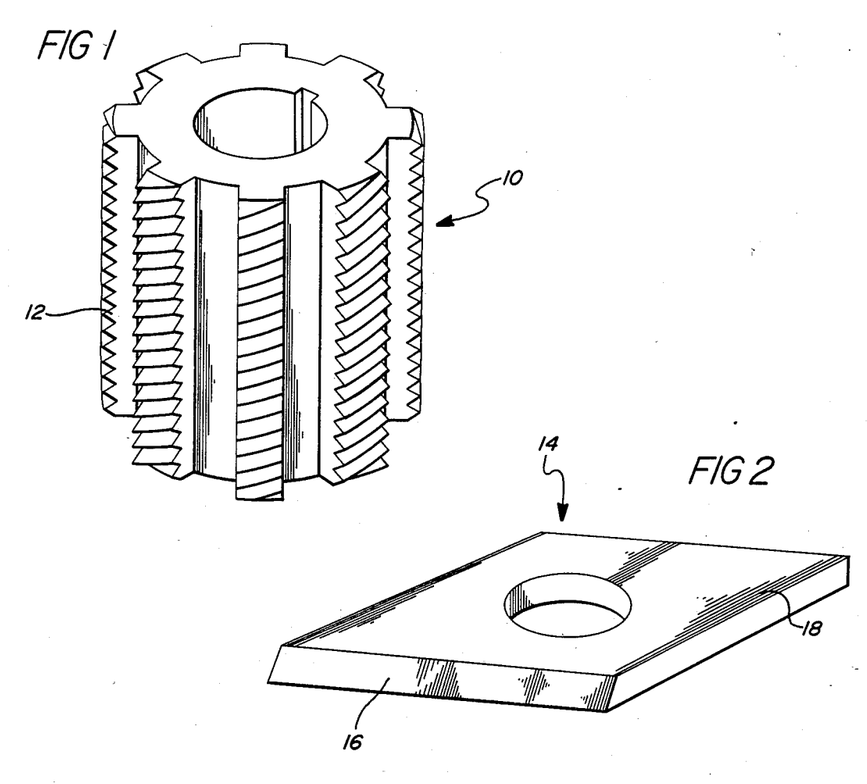
FIGS. 1-7 illustrate in perspective view various articles that can be coated in accordance with the invention.

In FIG. 1, there is illustrated a gear hob 10 which can be coated in accordance with the present invention. Gear hob 10 has a plurality of radially extending teeth 12 and is one example of a complex surface.

FIG. 2 is a perspective view of an insert tool 14 having a flank face 16 and a rake face 18. The substrate of insert tool can be coated over its entire surface with a wear resistant coating of disordered boron carbide.

Figure 3:
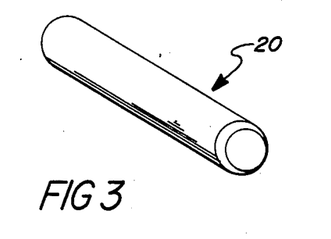

FIG. 3 is a perspective view of a bearing pin 20. Bearing pin 20 is an example of a relatively simple surface that can be coated with a wear resistant coating of boron and carbon.

Figure 4:
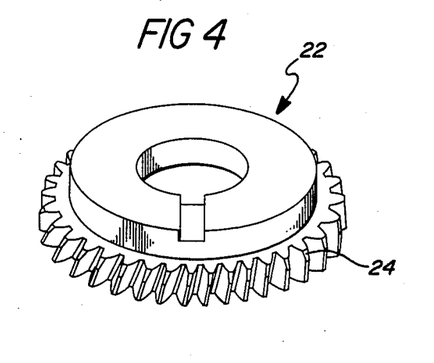

FIG. 4 illustrates a gear shaver tool 22 which is composed of a plurality of radially extending teeth 24. Gear shaver tool 22 illustrates another relatively complexly surfaced tool for which the method and coatings in accordance with the present invention are suitable.

Figures 5, 6, 7:
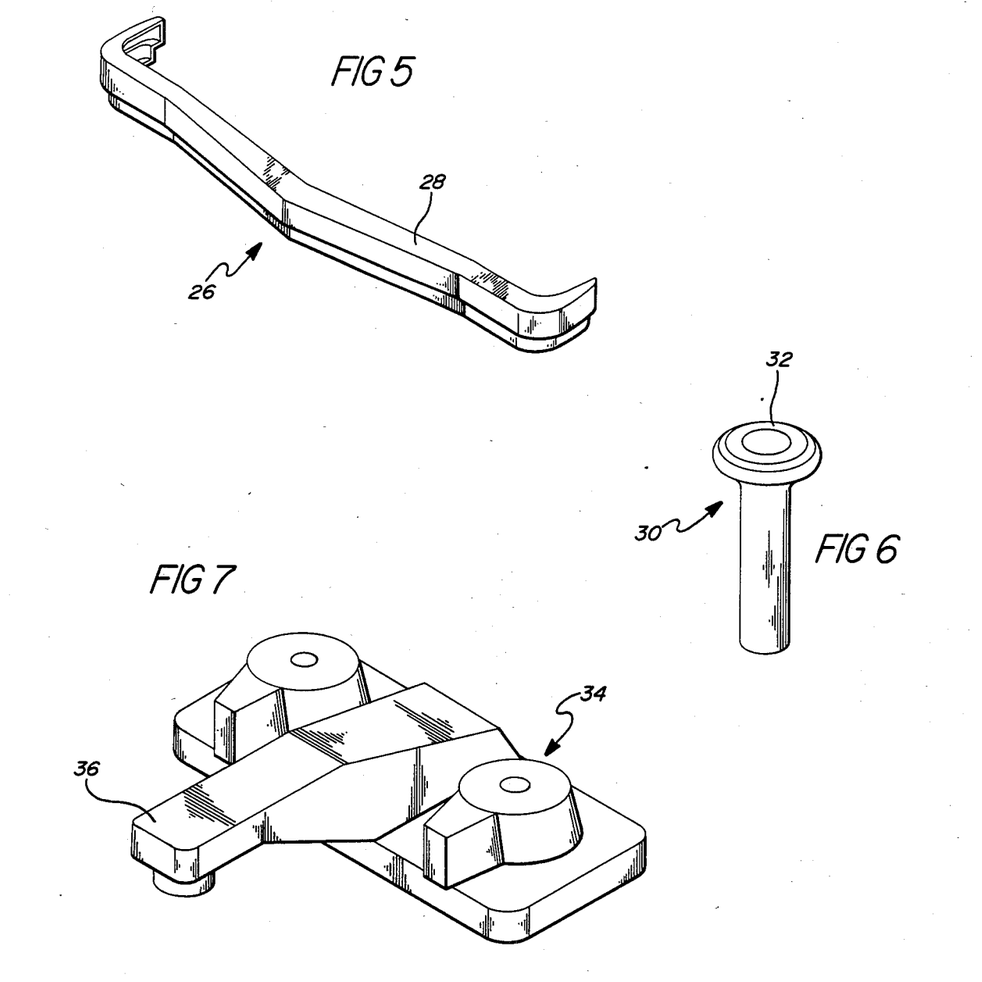

Referring now to FIGS. 5-7, several articles are depicted to which coatings in accordance with the invention can be applied primarily for decorative purposes. It is, of course, to be understood that the type of articles to which the coating may be applied is virtually limitless, and these illustrations are merely set forth by way of example. In FIG. 5, there is illustrated a steel automobile bumper 26 that can have a coating 28 in accordance with the invention on the surface thereof. Coating 28 is a thin grayish layer of substantially amorphous boron and carbon and is from about 2000 Å to about 5000 Å in thickness and has a high gloss.

In FIG. 6, a plastic automobile door lock button 30 is illustrated that can have a coating 32 in accordance with the invention on the surface thereof.

In FIG. 7, a water faucet 34 is illustrated having a coating 36 in accordance with the invention.

When the coating is used for decorative purposes, a protective overcoat layer may be provided over the coating. For most applications the protective overcoat will be substantially transparent and clear, although it could be colored, if desired. Any such type of material which does not deleteriously affect the boron and carbon coating to an unwanted degree can be used. For example, polymer resins can be used which are thermoplastic or thermosetting. Suitable polymer resins which can be selected from a wide group of materials. Included in this group are, for example, polyurethanes, vinyl polymers and copolymers, copolymers of vinylidene chloride and vinyl acetate, copolymers of vinylidene chloride and acrylonitride, copolymers of vinyl chloride and vinyl acetate, polycarbonates, polyamide, polyesters, ABS copolymers and the like. These materials are also suitable for use as a precoat over the substrate to provide a smoother surface. Any suitable method can be used to apply the overcoat or precoat layer. By way of illustration only, such methods include, for example, spraying, brushing, roller coating, dipping, spin coating, vacuum deposition, electrolysis, electrostatic spraying, or the like.

Figure 8:
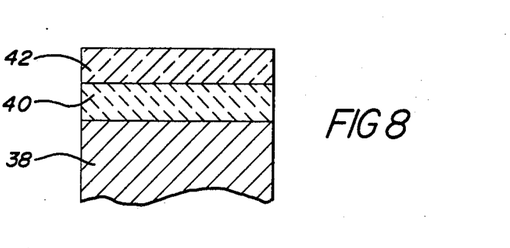
FIG. 8 illustrates in sectional view a coating in accordance with the invention having a transparent coating applied thereover.

Referring to FIG. 8, there is illustrated an enlarged cross-sectional view of a portion of a substrate 38 having a disordered boron and carbon coating 40 in accordance with the invention. Applied over the surface of coating 40 is a thin layer of a protective overcoat 42, which serves to protect coating 40 from impact. Protective overcoat 42 is a polymer resin that is substantially transparent.

Figure 9:
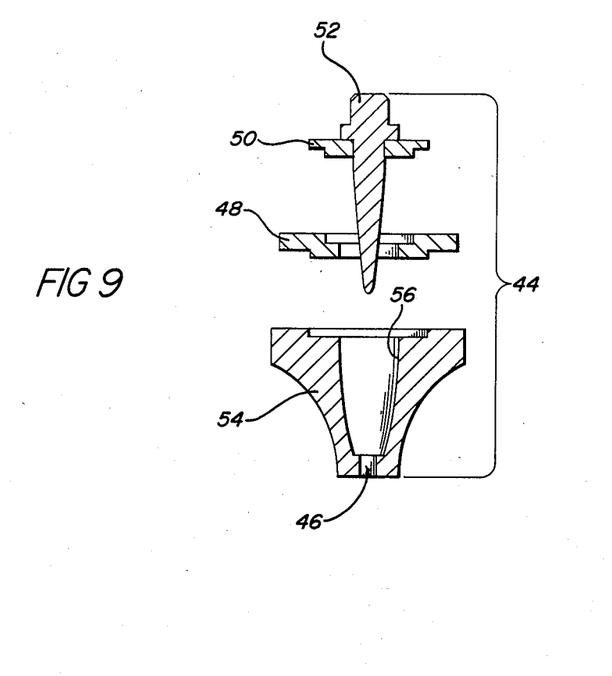
FIG. 9 illustrates in sectional view mold tool implements in accordance with the present invention.
Figure 10:
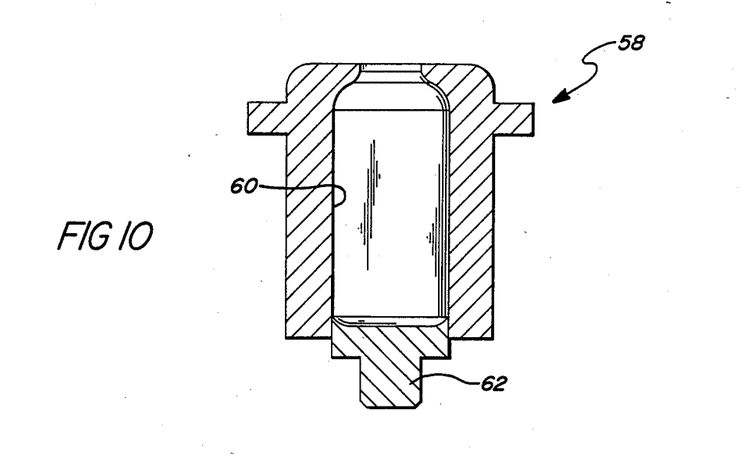
FIG. 10 illustrates in sectional view a blow mold tool in accordance with the present invention.
Figure 11:
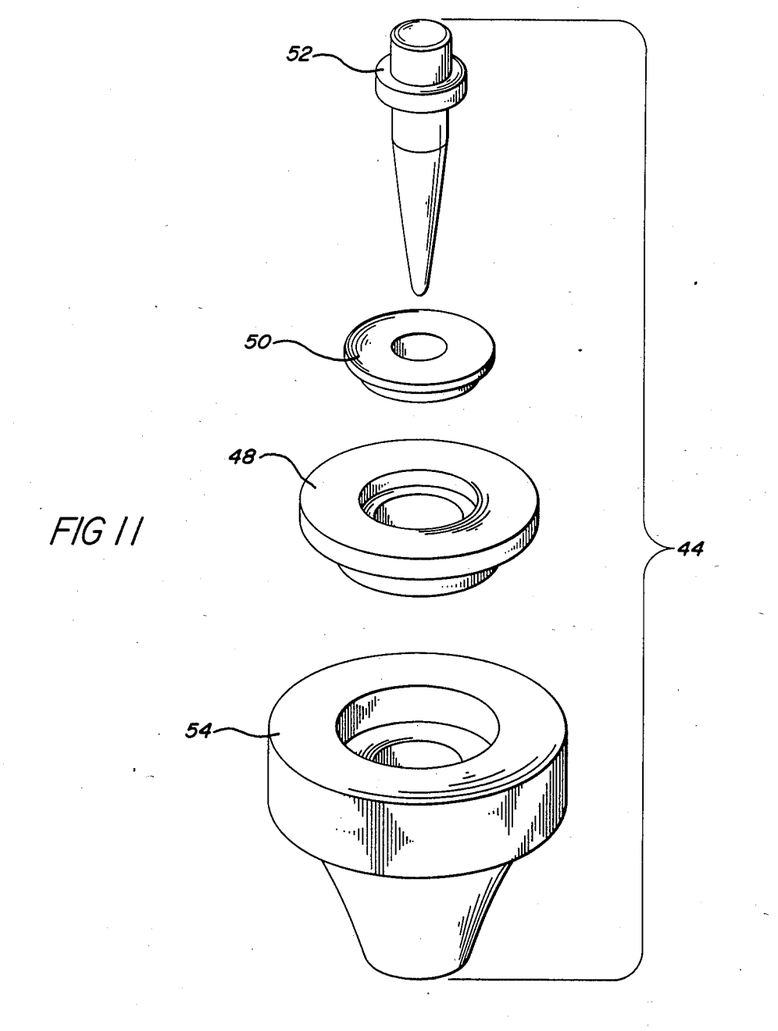
FIG. 11 illustrates in perspective view the mold tool implements of FIG. 9.

Referring to FIGS. 9-11, shown are various molding implements that include coatings in accordance with the invention. These are illustrated by way of example only and it is to be understood that the coating may be applied to virtually any type of molding or casting implement.

Referring specifically to FIG. 9, there is illustrated in sectional view mold implements for molding, such as with a press-blow machine. The mold implements include a parison or blank mold 44, an airing valve 46, a finish mold 48, a ring 50 and a plunger 52. The same implements are illustrated in FIG. 11 in perspective view, with like reference numerals indicating like elements. The wall 54 of parison mold 44 is cylindrical and the working surface 56 of parison mold 44 is coated with a disordered boron and carbon coating in accordance with the invention. Preferably, the entire working surface of parison mold 44, finish mold 48, ring 50 and plunger 52 will be coated with a disordered boron and carbon coating of the invention. Usually, for applications in which the coating is utilized in a mold implement, the thickness of the coating will be in the range of from about 0.08 microns to about 5 microns. The thickness of about 2½ microns is an especially desirable thickness. Typical mold implements such as those shown in FIGS. 9–12 may be constructed of cast iron. The disordered boron and carbon coatings of the invention are especially suitable for such materials and do not require an adherence or undercoating. However, it is to be understood that the coating can be utilized on virtually any type of material.

During operation of a press-blow process, finish mold 48 is placed on top of parison mold 44. Thereafter, a gob of moldable material is dropped into parison mold 44 and plunger 52 with ring 50 is introduced into parison mold 44 from above (not shown). After the parison is formed, it is removed from parison mold 44 and placed in a blow mold 58, shown in FIG. 10. Compressed air is then introduced into the interior of the parison which is then transformed into the shape defined by the interior of blow mold 58. Working surface 60 of blow mold 58 has a disordered boron and carbon coating in accordance with the invention thereon. Blow mold 58 also includes a bottom 62. The top portion of bottom 62 which forms the interior of the bottom of blow mold 58 also has a disordered boron and carbon coating in accordance with the invention.

The molding implements depicted in FIGS. 9–11 can be coated on their working surfaces by any suitable technique as described herein. Depending on the working surface configuration, it may be advantageous to build a specific molding section while coating the working surfaces prior to assembly of the mold. This would facilitate depositing the coating on the working surface in some cases, especially where the mold has a narrow entrance and a relatively wide cavity, such as shown in FIG. 10.

Use of the coatings on molding implements and the like is especially suited for glass molding, for example, and for molding other materials, including metals and polymers, especially where the temperatures encountered are less than the crystallization temperature of the coating. Usually, for glass molding, temperatures will be less than about 1000° C.

Generally, the KHN (50 grams) hardness of the boron carbide coatings in accordance with the present invention is about 4,700 kg/mm$^2$ as measured on a 50 micron thick (boron carbide) coating that was substantially amorphous with some microcrystalline material. Since the disordered coatings are generally relatively thin, direct measurement of a typically used thickness is impractical. It is expected that thinner coatings would have about the same hardness. However, in addition to being relatively hard, the coatings of the present invention generally also exhibit excellent lubricity. As a result, tools in accordance with the present invention have increased life and the use of such tools can result in an improved surface finish on parts machined therewith.

The present invention and its advantages can be more completely understood from the following examples:

EXAMPLE 1

A disordered coating in accordance with the invention was dc magnetron sputtered utilizing a target that was formed by hot pressing 99% pure, crystalline B$_4$C powder. The target was silver epoxy bonded to the backing plate and initially broken in by depositing for six hours dc at 300 watts, then for two hours rf at 500 watts and finally brought up to 1050 watts dc over 30 minutes and allowed to preclean at that voltage for an additional 30 minutes. A coating of approximately 50 micrometers of carbon and boron was formed. X-ray diffraction data indicated that the coating was substantially amorphous with some microcrystalline material.

Differential thermal analysis indicated that the crystallization temperature of the disordered boron carbide coating was about 1280° C.

EXAMPLE 2

An amorphous boron and carbon coating in accordance with the invention was DC magnetron sputtered utilizing a target that was formed by hot pressing 99% pure, crystalline B$_4$C powder. The coating was applied to an M2 high speed single point lathe tool and to M7 high speed steel drills. To provide an atomically clean surface, the tools were dc etched. The boron and carbon amorphous coating was applied by dc magnetron sputtering with a gas pressure of 6 microns argon and a dc bias voltage of 500 volts for about the initial 40% of the coating thickness and thereafter a bias voltage of 250 volts dc was applied for the remainder of the coating deposition. The total coating thickness on each tool was about 3.2 micrometers. X-ray defraction testing indicated that the coatings were amorphous.

The lathe tool and drills were subjected to tests to determine the life of coated tools versus uncoated tools. The lathe tool was utilized in a turning operation on cold rolled 1040 steel. The drills were subjected to a drilling test on gray cast iron plates having a Brinell Hardness Number of from 219 to 239. The turning and drilling tests did not utilize lubrication.

The lathe tool was utilized at a speed of 170 ft/min at a feed rate of 0.008 in/rev. The depth of cut was 0.050 inches. The lathe tool having the amorphous boron and carbon coating exhibited a tool life that was four times as long as the life of the same type of lathe tool used under the same conditions without any coating.

In the drilling tests, through holes were drilled in the gray cast iron plates which were ½ inch thick with full penetration of the point and shoulder of the drills. The feed rate was 0.0083 inches per revolution. The number of holes to catastrophic failure was taken as the tool life criterion. The following results were obtained in the drilling test:

| DRILL SPEED (ft/min) | TOOL LIFE RATIO (coated/uncoated) |
| --- | --- |
| 120 | 3 |
| 130 | 4 |
| 150 | 6 |
| 170 | 12 |

The foregoing results indicate a substantial improvement was obtained from the use of tools coated in accordance with the invention compared with uncoated tools.

EXAMPLE 3

A stainless steel plate was coated with an amorphous boron and carbon coating in accordance with the invention. The coating was applied to the stainless steel plate in accordance with the procedure set forth in Example 2. The coating had a thickness of about 3.2 micrometers.

The stainless steel plate having the coating thereon was subjected to an air atmosphere having a relative humidity of about 88% and a temperature of about 33° C. The exposure occurred for more than 56 days with no apparent spalling, degradation or loss of integrity of the coating.

EXAMPLE 4

A stainless steel plate was coated as set forth in Example 3. The coated stainless steel plate was subjected to the vapor of a cutting fluid that was being reflexed. The temperature of the vapor was about 100° C. and the exposure occurred for eight hours. The cutting fluid contained sulphur and chlorine additives of the type utilized to control the growth of bacteria. After the test, no visible change was apparent in the coating.

EXAMPLE 5

A chrome water faucet was coated in accordance with the invention by applying a boron and carbon coating by dc magnetron sputtering. The coating had a thickness of about 10,000 Å and was of an attractive gray color with a high gloss. The coating could not be visibly scratched by rubbing with steel wool.

Coatings of disordered boron and carbon of desired proportions can be made by sputtering and appropriately choosing the target composition. Also, multiple targets of different elements or compositions could be utilized. While the foregoing examples have shown production of the disordered coating materials by sputtering techniques, the invention is not so limited. Any method which produces a coating having the desired degree of disorder (amorphous, polycrystalline, microcrystalline or any combination thereof) can be utilized. By the term "amorphous" is meant a material which has long range disorder, although it may have short or intermediate order or even contain at times some crystalline inclusions.

It is to be understood that the coatings of the present invention are not limited to wear applications involving tools or decorative uses. The invention is useful on surfaces that may be subjected to wear, including, for example, and not as a limitation on the invention, bearings, engine parts, fittings, and other devices where friction or wear is encountered.

While this invention has been described in relation to its preferred embodiments, it is to be understood that various modifications thereof will be apparent to those of ordinary skill in the art upon reading this specification and it is intended to cover all such modifications as fall within the scope of the appended claims.

We claim:
1. A mold comprising:
(a) a hollow form defining a working surface for forming a moldable or castable material into a predetermined shape; and
(b) a thin coating over at least a portion of the working surface for contact with said material during molding, said coating consisting essentially of disordered boron and carbon.
2. The mold of claim 1 wherein said coating is formed by dc magnetron sputtering.
3. The mold of claim 1 wherein at least a portion of the coating is formed by bias sputtering.
4. The mold of claim 1 wherein said coating is formed by dc magnetron sputtering with a bias voltage being utilized during at least a portion of said sputtering.
5. The mold of claim 1 wherein said disordered boron and carbon comprises amorphous material.
6. The mold of claim 1 wherein said disordered boron and carbon comprises polycrystalline material.
7. The mold of claim 1 wherein said disordered boron and carbon comprises microcrystalline material.
8. The mold of claim 1 wherein said disordered boron and carbon material comprises at least one phase selected from the group consisting of amorphous, microcrystalline and polycrystalline phases.
9. The mold of claim 1 wherein said boron and carbon is substantially amorphous.
10. The mold of claim 1 wherein said coating comprises disordered boron carbide.
11. The mold of claim 1 wherein said coating has a composition on an atomic basis of $B_xC_{1-x}$ where x is from about 0.60 to about 0.90.
12. The mold of claim 1 wherein the thickness of the coating is in the range from about 0.20 to about 8 micrometers.
13. The mold of claim 1 wherein the thickness of said coating is in the range of from about 0.080 micrometers to about 5.0 micrometers.
14. The mold of claim 1 wherein the thickness of said coating is about 2.5 micrometers.
15. The mold of claim 1 wherein said coating is over substantially the entire working surface of the mold.
16. The mold of claim 1 wherein said hollow form comprises cast iron.
17. A method of molding an article comprising:
(a) providing a mold having a working surface that defines a predetermined shape, said working surface having a coating for contact with material to be molded during molding, said coating formed by sputtering while maintaining said working surface at a temperature permitting the formation of disordered boron and carbon and consisting essentially of disordered boron and said carbon, said coating over at least a portion of said working surface;
(b) placing a moldable material in said mold and forming said moldable material into the desired shape; and
(c) thereafter releasing the moldable material from the mold.
18. The method of claim 17 wherein the moldable material is glass.
19. The method of claim 18 wherein the glass is molded at elevated temperature, said elevated temperature being lower than the crystallization temperature of said coating.
20. The method of claim 19 wherein said elevated temperature is less than about 1000° C.
21. The method of claim 17 wherein said coating is formed by dc magnetron sputtering.
22. The method of claim 17 wherein at least a portion of the coating is formed by bias sputtering.
23. The method of claim 18 wherein said coating is formed by dc magnetron sputtering with a bias voltage being utilized during at least a portion of said sputtering.

24. The method of claim 17 wherein said disordered boron and carbon comprises amorphous material.

25. The method of claim 17 wherein said disordered boron and carbon comprises polycrystalline material.

26. The method of claim 17 wherein said disordered boron and carbon comprises microcrystalline material.

27. The method of claim 17 wherein said disordered boron and carbon material comprises at least one phase selected from the group consisting of amorphous, microcrystalline and polycrystalline phases.

28. The method of claim 17 wherein said boron and carbon is substantially amorphous.

29. The method of claim 17 wherein said coating comprises disordered boron carbide.

30. The method of claim 17 wherein said coating has a composition on an atomic basis of $B_xC_{1-x}$ where x is from about 0.60 to about 0.90.

31. The method of claim 17 wherein the thickness of the coating is in the range from about 0.20 to about 8 micrometers.

32. The method of claim 17 wherein the thickness of the coating is in the range of from about 0.080 to about 5.0 micrometers.

33. The method of claim 17 wherein said coating is over substantially the entire working surface of the mold.

34. The mold of claim 1 wherein said coating is formed by sputtering.

* * * * *